US011874285B2

(12) United States Patent
Kjaer et al.

(10) Patent No.: US 11,874,285 B2
(45) Date of Patent: Jan. 16, 2024

(54) METHOD FOR CALIBRATING A DEVICE FOR MEASURING THE CONCENTRATION OF CREATININE

(71) Applicant: Radiometer Medical ApS, Bronshoj (DK)

(72) Inventors: Thomas Kjaer, Smorum (DK); Thomas Pedersen Nyggard, Herlev (DK)

(73) Assignee: Radiometer Medical ApS, Bronshoj (DK)

(*) Notice: Subject to any disclaimer, the term of this patent is extended or adjusted under 35 U.S.C. 154(b) by 184 days.

(21) Appl. No.: 15/533,692

(22) PCT Filed: Dec. 14, 2015

(86) PCT No.: PCT/EP2015/079592
§ 371 (c)(1),
(2) Date: Jun. 7, 2017

(87) PCT Pub. No.: WO2016/096725
PCT Pub. Date: Jun. 23, 2016

(65) Prior Publication Data
US 2017/0315139 A1  Nov. 2, 2017

(30) Foreign Application Priority Data
Dec. 18, 2014 (DK) ............ PA 2014 00738

(51) Int. Cl.
*G01N 33/70* (2006.01)
*G01N 27/327* (2006.01)
*C12Q 1/00* (2006.01)

(52) U.S. Cl.
CPC ............ *G01N 33/70* (2013.01); *C12Q 1/005* (2013.01); *C12Y 105/03001* (2013.01);
(Continued)

(58) Field of Classification Search
CPC ............ G01N 33/70; G01N 27/3273; G01N 27/3274; G01N 2333/90683;
(Continued)

(56) References Cited

U.S. PATENT DOCUMENTS 6,233,471 B1* 5/2001 Berner ............... A61B 5/14532
600/345
2004/0072277 A1* 4/2004 Schaffar ............... C12Q 1/001
435/25
(Continued)

FOREIGN PATENT DOCUMENTS

CN 103748458 A 4/2014
CN 103748459 A 4/2014
(Continued)

OTHER PUBLICATIONS

ABL800 Flex Reference Manual, Radiometer, pp. 1-1-7-18 (2012) (Year: 2012).*
(Continued)

*Primary Examiner* — Joshua L Allen
*Assistant Examiner* — Vivian A Tran
(74) *Attorney, Agent, or Firm* — FINNEGAN, HENDERSON, FARABOW, GARRETT & DUNNER, LLP

(57) ABSTRACT

A method of calibrating a device for measuring the concentration of creatinine using one or more calibration solutions, the method comprising: receiving concentrations at an initial time of creatine, Cr, and/or creatinine, Crn, of the one or more calibration solutions; receiving outputs of the measuring device at the end time; calculating the concentration of Cr and/or Crn in the calibration solutions at an end time using a temperature model, wherein the temperature model indicates an estimation of the temperature of the calibration solutions from the initial time to the end time, and wherein
(Continued)

the temperature model includes a variable parameter; and determining a relationship between the outputs of the measuring device and the calculated concentrations of Cr and/or Crn.

12 Claims, 6 Drawing Sheets

(52) U.S. Cl.
CPC .... *C12Y 305/0201* (2013.01); *G01N 27/3274* (2013.01); *G01N 27/3273* (2013.01); *G01N 2333/90683* (2013.01); *G01N 2333/986* (2013.01)

(58) Field of Classification Search
CPC .. G01N 2333/986; C12Q 1/001; C12Q 1/005; C12Q 1/32; C12Q 1/34; C12Y 105/03001; C12Y 305/0201; C12N 9/0034
See application file for complete search history.

(56) References Cited

U.S. PATENT DOCUMENTS

| | | | |
|---|---|---|---|
| 2006/0275859 A1* | 12/2006 | Kjaer | C12Q 1/002 |
| | | | 435/25 |
| 2006/0275860 A1* | 12/2006 | Kjaer | C12Q 1/34 |
| | | | 435/27 |
| 2009/0045056 A1 | 2/2009 | Berberich et al. | |
| 2009/0119047 A1* | 5/2009 | Zelin | G01K 3/04 |
| | | | 702/82 |
| 2012/0181189 A1 | 7/2012 | Merchant | |
| 2013/0000378 A1 | 1/2013 | Martin et al. | |
| 2013/0002279 A1* | 1/2013 | Martin | G01N 27/3274 |
| | | | 324/750.3 |
| 2017/0363567 A1* | 12/2017 | Kjaer | G01N 27/3274 |

FOREIGN PATENT DOCUMENTS

| | | |
|---|---|---|
| EP | 0 066 552 A1 | 12/1982 |
| JP | 2004-506224 A | 2/2004 |
| JP | 2010-539492 A | 12/2010 |
| WO | WO 95/22602 | 8/1995 |
| WO | WO 99/40430 | 8/1999 |
| WO | WO 2005/052596 A1 | 6/2005 |
| WO | WO 2011/037702 A1 | 3/2011 |
| WO | WO 2014/006406 A1 | 1/2014 |

OTHER PUBLICATIONS

Cannan et al., The creatine-creatinine equilibrium. The apparent dissociation constants of creatine and creatinine, Biochemical Journal, vol. 22, Issue 4, pp. 920-929 (1928) (Year: 1928).*
Diamond, Temperature and Ph Dependence of the Cyclization of Creatine: A Study Via Mass Spectrometry, Theses, Dissertations and Capstones, Paper 564, pp. 1-56 (2005) (Year: 2005).*
Edgar et al., The Kinetics of the Conversion of Creatine into Creatinine in Hydrochloric Acid Solutions, Journal of the American Chemical Society, vol. 45, Issue 10, pp. 2242-2245 (1923) (Year: 1923).*
Anderson, Geoffrey et al., "Determination of Product Shelf Life and Activation Energy for Five Drugs of Abuse," Clinical Chemistry, vol. 37, No. 3, pp. 398-402 (1991).
Porter, William R, "Thermal Accelerated Degradation and Storage Temperature Design Space for Liquid Products," Journal of Validation Technology, pp. 73-92 (2012).
International Search Report for International Application No. PCT/EP2015/079592, dated Aug. 2, 2016.
Written Opinion of the International Search Authority for International Application No. PCT/EP2015/079592.
Chen, Ping et al., "Sensitive Electrochemical Detection of Creatinine at Disposable Screen-Printed Carbon Electrode Mixed with Ferrocenemethanol," Int. J. Electrochem. Sci., vol. 8, pp. 8931-8939 (2013).
ABL800 Flex Operator's Manual, Jun. 2012, Radiometer (438 pages).
ABL800 Flex Reference manual, Jun. 2012, Radiometer (312 pages).
Edgar, G. et al., "The Equilibrium Between Creatine and Creatinine, in Aqueous Solution. The Effect of Hydrogen Ion," *J. Am. Chem. Soc.*, vol. 47, pp. 1179-1188 (1925).

* cited by examiner

METHOD FOR CALIBRATING A DEVICE FOR MEASURING THE CONCENTRATION OF CREATININE

This application is a national stage filing under 35 U.S.C. § 371 of International Application No. PCT/EP2015/079592, filed on Dec. 14, 2015, which claims priority of Danish Patent Application No. PA 2014 00738, filed Dec. 18, 2014. The contents of these applications are each incorporated herein by reference.

FIELD OF THE INVENTION

The invention relates to methods for calibrating creatinine measuring devices, and calibration solutions for use in those methods.

BACKGROUND

Techniques for measuring the concentration of creatinine (Crn) and creatine (Cr) are useful in medicine, for example in monitoring renal disease. The concentration of Cr (cCr) and the concentration of Crn (cCrn) in an aqueous solution can be determined by amperometric measurement. Two sensors are used in the measurement of cCrn: the Crea A sensor, which detects Cr; and the Crea B sensor, which detects both Cr and Crn. The cCrn is based on a difference between the Crea A and Crea B sensor measurements.

In order to determine cCrn in unknown samples with sufficient accuracy, the Crea A and Crea B sensors must be calibrated regularly in order to determine their actual sensitivities. The sensors can be calibrated using two aqueous calibration solutions of known cCrn and cCr. However, a problem with such calibration solutions is that cCr and cCrn are not fixed. Rather, when in aqueous solution, Crn can be converted into Cr and vice versa by water hydrolysis and elimination respectively, as indicated by the double arrow in the reaction equation in Scheme 1, where T is the temperature at which the reaction occurs and $k_1$ and $k_2$ are the rate constants for the hydrolysis and elimination reactions respectively.

Scheme 1

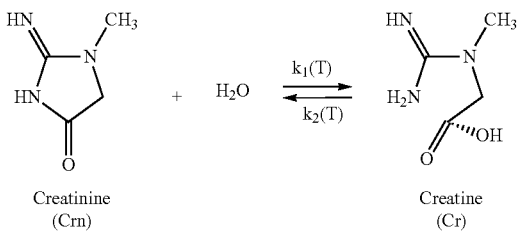

Creatinine (Crn)      Creatine (Cr)

After a sufficient period of time at a constant temperature the mixture will reach a dynamic equilibrium in which cCr and cCrn are constant. However, changes to the temperature of the solution will shift the equilibrium ratio, and therefore the cCr and cCrn will change.

A calibration solution having known cCr and cCrn in equilibrium ratios, can be generated by adding the enzyme creatinine amidohydrolase (CA) to a solution of known sum concentration of Cr and Crn, and then allow that solution to equilibrate by maintaining the solution at a specific temperature for about one hour. The CA facilitates equilibration. Once equilibrium is reached at a given temperature, the cCr and cCrn can be determined simply by reference to the known equilibrium constants at the given temperature.

WO 2005/052596 discloses a reference solution for quality control on a medical analyser and a kit for holding the reference solution. The kit comprises a container with a first and a second compartment, wherein the first and the second compartment may be separated by a thin wall, which may be broken upon exertion of manual pressure, which will cause the liquids of the first and second compartments to mix. The first compartment comprises a buffer, and the second compartment comprises two chemical compounds and a catalyst. When the two compounds, the catalyst and the buffer is mixed, a thermodynamic equilibrium is reached more rapidly allowing the solution to be used as quality control reference solution within hours, when conditioned at 25° C., whereas the solution would otherwise have to be conditioned for much longer, if no catalyst was used.

For sensors responding linearly to changes in both cCr and cCrn it is required that the chosen compositions of the two calibration solutions result in a linearly independent equation system, i.e., $cCr_{CalX}=m \cdot cCr_{CalY}$ and $cCrn_{CalX}=n \cdot cCrn_{CalY}$ with $m \neq n$ is required. Hence, only one of the calibration solutions can contain Cr and Crn at their equilibrium concentrations unless stored at two different temperatures. However, the best sensor calibration may be obtained by using one solution of essentially pure Cr and one solution of essentially pure Crn.

Calibration solutions having known cCr and cCrn in non-equilibrium ratios can be prepared by dissolving a known quantity of dry powder containing known quantities of Cr and Crn in a known volume of water, or other aqueous medium.

Typically, the calibration solution is kept at between 15° C. to 32° C., which allows for accurate calculations for solutions less than 14 days old, even when approximating this to be at a constant temperature. Therefore, existing methods are sufficiently accurate to enable the calculation of cCr and cCrn for calibration solutions having a short usage period (i.e. $t_{age}<14$ days).

Another alternative is to produce an acidic creatinine solution, this is thermodynamically stable and can thus be maintained during storage. This solution can then be mixed with a buffer-solution immediately before use to obtain a calibration solution of essentially pure Crn with a known pH and cCrn. This method corresponds to the method disclosed in the US2004/0072277. A problem with this approach is that it is difficult to produce a homogeneous mixture if the two solutions are contained in sealed airtight pouches. Additionally, the mixing process will also require pumping means if automatic mixing is required and/or if the pouches are part of a closed system, such as a cassette based solution pack. Furthermore, it is not advisable to let the solution pass through the sensor chamber, since the CA enzyme may leak out of the creatinine sensors, for example, and into the solution thereby destroying the non-equilibrium conditions. To prevent that could necessitate a separate channel for liquid transport.

In both cases, having a 14 day time limit for the accuracy of the calibration solution is disadvantageous in that frequent replacement is required, which is uneconomical and inconvenient for the end user. Furthermore, the short usage period may be reduced even further because the end user may have to wait several days for the solution to be delivered from the manufacturer. Alternatively the end user may be obliged to prepare the calibration solution at the point of use (e.g. hospital), which introduces additional work for the end user as well as the risk of inaccuracies, for example in weighing the Cr and Crn powder and measuring the volume of solvent or by uneven mixing. An unmet need exists for an approach enabling the use of calibration solutions having a $t_{age}$>14 days.

SUMMARY OF THE INVENTION

In a first aspect of the present invention, the applicant makes available a method of calibrating a device for measuring the concentration of creatinine using one or more calibration solutions, the method comprising: receiving concentrations at an initial time of creatine, Cr, and/or creatinine, Crn, of the one or more calibration solutions; receiving outputs of the measuring device at the end time; calculating the concentration of Cr and/or Crn in the calibration solutions at an end time using a temperature model, wherein the temperature model indicates an estimation of the temperature of the calibration solutions from the initial time to the end time, and wherein the temperature model includes a variable parameter; and determining a relationship between the outputs of the measuring device and the calculated concentrations of Cr and/or Crn.

By using a temperature model of the calibration solutions, it is possible to accurately calibrate the sensors even when the exact temperature profile the solutions have experienced is unknown over 14 days or more. The customer is not restricted to utilise the calibration solutions within a short time span after receiving the calibration solutions, as a temperature model allows the customer to store the solutions at a range of temperatures, while still providing accurate calibrations. By providing a model for the temperature profile, the actual temperature the solutions experienced need not be known, thereby avoiding the need for constantly-recording temperature sensors with the calibration solutions.

In some example embodiments the measuring device includes a sensor for measuring creatine in one or more of the calibration solutions.

In some example embodiments the measuring device includes a sensor for measuring creatinine in one or more of the calibration solutions.

In some example embodiments the measuring device includes a sensor for measuring creatine and creatinine in one or more of the calibration solutions.

In some example embodiments the measuring device is an amperometric measuring device.

In some example embodiments the method further comprises determining the temperature model by calculating the variable parameter, wherein said calculating comprises finding the solution to an analytic expression comprising rate equations, the temperature model, and outputs from the measuring devices.

In some example embodiments the analytic expression is derived from an integration of the rate equations for the temperature model, wherein rate constants in the rate equations are derived from the Arrhenius equations.

In some example embodiments, the temperature model comprises an average temperature from the initial time to the end time, and the variable parameter is the average temperature.

In some example embodiments, the temperature model comprises a temperature at the initial time, and a different temperature at an intermediate time, and wherein the variable parameter is the intermediate time.

In some example embodiments the determining a relationship between the measuring device outputs and the calculated concentrations of Cr and Crn comprises calculating sensor sensitivities of the measuring devices.

In some example embodiments the method comprises determining concentrations of Cr and/or Crn in a sample based on the calculated sensor sensitivities of the measuring devices and measuring device outputs.

In some example embodiments the end time is greater than 14 days after the initial time.

According to another aspect of the present invention, a computer readable medium is provided comprising instructions which when executed by one or more processors of an electronic device, cause the electronic device to operate in accordance with any of the aforementioned methods.

According to another aspect of the present invention, an electronic device is provided comprising: one or more processors; and memory comprising instructions which when executed by one or more of the processors cause the electronic device to operate in accordance with any of the aforementioned methods.

According to another aspect of the present invention, a package is provided comprising one or more calibration solutions, the package being suitable for use with any of the aforementioned methods or aforementioned electronic devices.

In some example embodiments, the package further comprises an indication of the initial time and the concentrations at the initial time of creatine (Cr) and creatinine (Crn) of the two or more calibration solutions.

BRIEF DESCRIPTIONS OF DRAWINGS

Examples of the present proposed apparatus will now be described in detail with reference to the accompanying drawings, in which.

DETAILED DISCLOSURE

Figure 1:
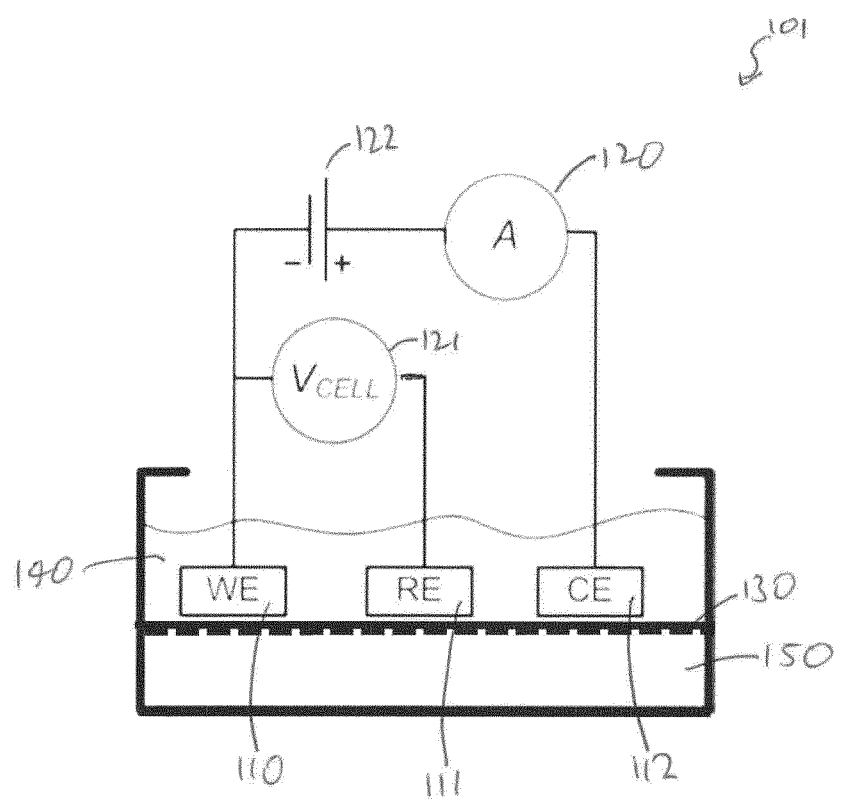
FIG. 1 is a schematic diagram of an example of an amperometric measuring system.

Reference will now be made to FIG. 1 which is a schematic diagram of a three-electrode amperometric measuring system 101. An amperometric measuring system may have at least two electrodes: a working electrode (WE) 110 and a combined counter and reference electrode (CE/RE). For the three-electrode amperometric measuring system 101, the functions of the CE/RE electrode are split into two separate electrodes: the reference electrode (RE) 111 and the counter electrode (CE) 112. The example amperometric measuring system 101 also includes an ammeter 120, a voltmeter 121 and a voltage source 122 and the electrolyte solution 140.

The WE 110 is a positively charged electrode where an oxidation reaction occurs. The RE 111 is typically made of Ag/AgCl and is able to maintain a stable potential, especially if no current runs through it, thus the need for a CE 112 for passing the current from the WE 110 back to the electrolyte solution 140. The electrolyte solution 140/sample 150 provides a current path between the three electrodes. The membrane 130 selectively converts the analyte to a substance that selectively is allowed to pass through from the sample 150. The voltage source 122 applies the necessary potential for maintaining the desired reduction or oxidation reaction, this is controlled by the voltmeter 121. The ammeter 120 measures the resulting current flowing through the electrical circuit.

The amperometric measuring system shown in FIG. 1 is an illustrative example, and several other implementations are envisioned. For example, the amperometric measuring system could be a two electrode system as mentioned above.

The magnitude of an electrical current flowing through the electrode chain is proportional to the concentration of the substance being oxidized (or reduced) at the WE 110. Ideally, when knowing the proportionality constant relating the electrical current to a concentration, the concentration in any given sample can be obtained by measuring the electrical current generated by that particular sample.

To illustrate the measuring process in an amperometric measuring system, we assume that: The sample 150 contains species B which, in the membrane 130, is selectively converted to species A, which can be oxidized at the WE 110 (anode) to $A^+$; and the electrolyte 140 contains species X which is reduced at the CE 112 (cathode) to $X^-$. We assume also that the membrane 130 allows only species A to pass from the sample into the electrolyte solution 140.

As an appropriate potential is applied across the electrodes, A is oxidized at the WE 110 according to the following reaction:

$$A \rightarrow A^+ + e^-$$

The oxidation of A produces a flow of electrons. To complete the electrical circuit a reduction reaction where electrons are consumed is necessary. Therefore species X is reduced at the CE 112 according to the following reaction:

$$X + e^- \rightarrow X^-$$

The magnitude of the current flowing through the circuit is proportional to the concentration of the analyte being oxidized. The analyser can therefore automatically calculate the concentration of the analyte in the sample given species X is in excess.

The term sensor refers to a complete amperometric measuring system, as shown in FIG. 1 excluding the sample 150.

Crn is not stable in aqueous solutions, e.g. blood, where it is reversibly converted into Cr (see Scheme 1). To measure cCrn, the present invention utilizes a two-sensor system where one sensor (Crea A) detects Cr only, and the other sensor (Crea B) detects both Cr and Crn. By means of a difference measurement it is possible to obtain the cCrn value.

The sensor is protected by a multilayer membrane 130 consisting of at least three functional layers, namely the outer membrane layer permeable to Crn and Cr; the middle enzyme layer, and the inner membrane layer permeable to $H_2O_2$.

Crn and Cr molecules diffuse across the outer membrane layer. The enzymes creatinine amidohydrolase, creatine amidinohydrolase and sarcosine oxidase are immobilized between the inner and outer membrane layers. The Crea A sensor contains only creatine amidinohydrolase and sarcosine oxidase, and so detects only Cr. In the Crea A sensor, the enzymatic cascade changes Cr as follows:

Creatine+$H_2O \rightarrow$ sarcosine+urea (creatine amidinohydrolase)

Sarcosine+$H_2O$+$O_2 \rightarrow$ glycine+formaldehyde+$H_2O_2$ (sarcosine oxidase)

The Crea B sensor contains all three enzymes creatinine amidohydrolase, creatine amidinohydrolase and sarcosine oxidase, and so detects both Crn and Cr. In the enzymatic cascade Crn/Cr changes as follows:

Creatinine+$H_2O \leftrightarrow$ creatine (creatinine amidohydrolase)

Creatine+$H_2O \rightarrow$ sarcosine+urea (creatine amidinohydrolase)

Sarcosine+$H_2O$+$O_2 \rightarrow$ glycine+formaldehyde+$H_2O_2$ (sarcosine oxidase)

For both the Crea A and the Crea B sensors the enzyme reactions lead to identical end-products, one of which is $H_2O_2$ that can diffuse across the inner membrane layer to the WE 110 (preferably platinum). By applying a sufficiently high electrical potential to the electrode chains of the Crea A and Crea B sensors, $H_2O_2$ can be oxidized at the WE 110:

$$H_2O_2 \rightarrow 2H^+ + O_2 + 2e^-$$

To complete the electrical circuit, electrons are consumed in reduction reactions at the CE 112 thereby maintaining a charge balance between the WE 110 and the CE 112.

The oxidation of $H_2O_2$ produces an electrical current (I) proportional to the amount of $H_2O_2$, which in turn is directly related to the amount of Cr for the Crea A and the amount of Cr and Crn for the Crea B sensors according to the sensor response models:

$$I^A = S_{Cr}^A \cdot cCr \qquad \text{Equation 1}$$

$$I^B = S_{Cr}^B \cdot cCr + S_{Crn}^B \cdot cCrn \qquad \text{Equation 2}$$

Where $I^A$ and $I^B$ are the electrical currents produced at the Crea A and Crea B sensors respectively; $S_{Cr}^A$ and $S_{Cr}^B$ are the sensitivity constants relating current (I) to Cr concentration in the Crea A and Crea B sensors respectively and $S_{Crn}^B$ is the sensitivity constant relating current (I) to Crn concentration in the Crea B sensor.

The proportionality constants, S, relating currents to concentrations are typically referred to as sensitivities. The constants are determined by calibrating the sensors. The current (signal) of each sensor is measured by ammeters 120 in the analyser. If sensor sensitivities S are known, the unknown Crn concentration in a given sample is readily determined from the equations above.

The changes in cCr and cCrn relative to the last known values of cCr and cCrn can be calculated based on reaction rate equations and rate constants described by the Arrhenius equation. To make the calculation it is necessary to know the period of time elapsed since the cCr and cCrn was last known ($t_{age}$), and the temperature experienced by the solution during that period.

One way of making accurate estimations of cCr and cCrn when the calibration solution has experienced a range of temperatures, is to record the changes in temperature since the last concentration measurements. For example, when the calibration solutions are shipped, the calibration solution packs may include a temperature measurement device and a means for recording the changes in temperature.

One example implementation would include a temperature probe that records the temperature of the solutions at regular intervals into computer memory, so that when the solutions need to be calibrated, the memory can be accessed to determine the temperatures experienced. The combination of a temperature probe and memory for recording the recorded temperatures may be referred to herein as a temperature logger.

Knowing the historic changes in temperature, it is possible to accurately calculate the changes in concentration from the initial concentrations recorded to a calculated concentration at the time of calibration. For example, it is possible to calculate the change in cCrn and cCr over time based on the reaction rate equations and the rate constants described by the Arrhenius equation, and applied to the recorded temperatures over time.

As each solution pack would require a temperature logger, to reduce the costs it may be beneficial to use a low-cost temperature probe. While a low-cost temperature probe may lead to inaccurate temperature measurements, the temperature probe may be calibrated with a more accurate temperature probe. This calibration may involve comparing measurements by the low-cost and reference temperature probe for one temperature or over a range of temperatures to determine if there is a difference between the measurements. If a difference is determined, the recorded temperatures in the memory may be offset by this difference. The offsetting of recorded temperatures may be applied to readings already recorded, or may be applied to all subsequent recordings of temperature.

Temperature loggers packaged with solution packs can be used to provide an accurate measurement of temperature changes while the solution pack is being stored and transported, and eventually can be used to help calibrate sensors. Once the calibration solutions have reached their destinations, the sensors can been calibrated using the accompanying temperature loggers, and the temperature may then be continued to be monitored by a more accurate temperature logger to ensure that the sensor sensitivities are kept up to date. The more accurate temperature logger may be part of a measurement station or may be part of a permanent installment of the end user.

Surprisingly it has been found that in one embodiment calculating the conversions in the calibrators using a temperature logger with a temperature offset from the real temperature, and a thermal exposure that does not quite resemble the temperature profile experienced by the calibration solutions still can provide an acceptable estimate of the Cr and Crn concentrations in the calibrators. Therefore, such calibration of the temperature probes may not be required, and the low-cost temperature probes may be used. Using a temperature logger as an estimate of the exact temperature profile can provide sufficient data for estimating the Cr and Crn concentrations in the calibrators.

While using one or more temperature measurement devices and recording the measurements can lead to very accurate calculations for end concentrations, it may be advantageous to calculate similarly accurate results without the use of temperature probes or memory in order to reduce the costs of each pack of calibration solutions. One such method involves using temperature models to estimate the changes in temperatures experienced.

Figure 2:
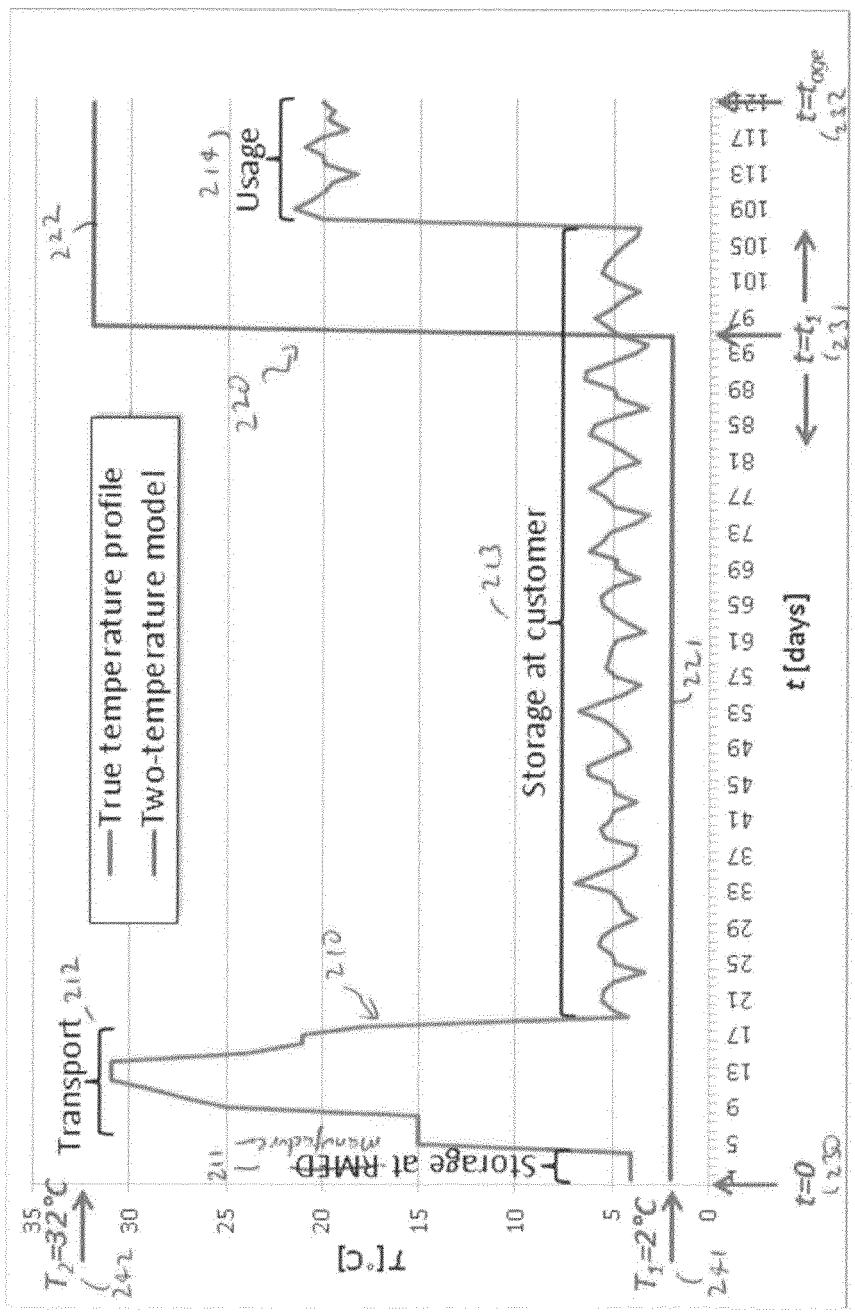
FIG. 2 is a graph showing the temperature variation of calibration solutions and a corresponding two-temperature model estimating the temperature variation.

FIG. 2 is a graph showing an example temperature profile of calibration solutions and a corresponding two-temperature model estimating the temperature variation. The true temperature profile 210 shows the actual temperature variation from an initial time 230 (t=0) to an end time 232 (t=$t_{age}$). In this example, the temperature starts at a low 4° C. for an initial period of 4 days in storage at the manufacturer 211. When the calibrations solutions are transported, the temperature rises to a higher temperature of 31° C. for a period of roughly 14 days 212. After transporting 212 the calibration solutions, they are stored at a low temperature (roughly 5° C.) with the customer 213 for a period of roughly 76 days. In this example, the customer takes the calibration solutions out of storage in order to use them over a period of 14 days 214, during which time, the calibration solutions are kept at a higher temperature of roughly 20° C.

While the end user will be aware of the temperature of the calibration solution if the user prepared it themselves by combining an aqueous medium of known temperature and Cr and Crn powder, the user will not be aware of the temperature profile from the point of production up to usage if prepared by the manufacturer. As shown in FIG. 2, the true temperature profile 210 can be very complicated, with large temperature fluctuations over a long period of time. In the past, such temperature fluctuations have made it difficult to accurately calculate the concentration levels of the calibration solutions.

The applicant has surprisingly identified that although a temperature profile is not necessarily known by the customer, the complex temperature profile can be modelled by a much simpler temperature model. An example temperature model, a two-temperature model 220, is indicated in FIG. 2. The complex temperature profile is modelled as having a low temperature of $T_1=2°$ C. 241 for a first time period 221 from an initial time t=0 230 to an intermediate time t=$t_1$ 231, and then having a high temperature of $T_2=32°$ C. 242 for a period 222 from the intermediate time t=$t_1$ 231 to an end time t=$t_{age}$ 232. While the two-temperature model 220 in FIG. 2 does not exactly match the true temperature profile 210, it provides a functional estimation of the changes in temperature.

The value of $t_1$ can be optimised to compensate for any discrepancies between the true temperature profile 210 and the two-temperature model 220. For example, although the final increase in temperature in the true temperature profile 210 occurs at about 107 days, the corresponding increase in temperature of the two-temperature model 220 occurs at an earlier time t=$t_1$=95 days. This earlier time for $t_1$ is earlier than the actual increase in temperature to compensate for the large increase in temperature during the initial transport phase 212. Similarly, if the temperature values $T_1$ and $T_2$ are chosen to be too high or too low, the value of $t_1$ can be adjusted to compensate for this as well.

The true temperature profile can be simplified to a multiple-temperature model as the pattern of storage, transport and usage conditions for the creatinine/creatine solutions follow similar patterns. Table 1 shows the estimated time and temperature ranges for an example calibration solution supporting cCrn measurements.

TABLE 1

| | Max. time [days] | Temperatures [° C.] |
|---|---|---|
| Storage at manufacturer | 56 | 2-8 |
| Transport from manufacturer to customer | 14 | 2-32 |
| Storage at customer | 108 (~3½ months) | 2-8 |
| Usage | 14 | 15-32 |

Other multiple-temperature models could be used. For example, a temperature model with three or more temperatures may be used. Rather than discrete step changes in temperature, progressive cooling and heating of the temperatures could be incorporated into the model using simple exponential functions, or fluctuations could be incorporated into the model using sinusoidal functions, for example.

In the example embodiment provided, a two-temperature model is used as it provides a simple illustration of the proposed solution. In this example embodiment, the following calibrators, Cal2 and Cal3, are used for calibrating the Crea A and Crea B sensors:

TABLE 2

| At time: $t_{production}$ | Cal2 | Cal3 |
|---|---|---|
| cCr [µM] | 0 | 500 |
| cCrn [µM] | 500 | 0 |
| Sensor | Crea B | Crea A and Crea B |

In addition to the Cr and Crn, calibrators Cal2 and Cal3 may also contain buffers, salts, preservatives and detergents. For the purposes of the proposed method, the concentrations of only Cr and Crn in the calibrators will be reviewed.

In the example embodiment presented herein, the concentrations of both Cr and Crn are being determined through the use of two calibration solutions and two sensors. However, it is envisioned that the proposed method may be used to calculate only the Cr concentrations or only the Crn concentrations. If concentrations of just one substance is determined (Cr or Crn), then only one specific sensor (Cr or Crn) and two calibration solutions are needed.

As shown in Scheme 1, Crn can be converted into Cr and vice versa by water hydrolysis and elimination in a reversible reaction. This reversible conversion reaction starts immediately when either of the two species are dissolved in water and it will continue with a higher rate in one direction until the system reaches thermodynamic equilibrium, i.e., until Crn and Cr reach their mutual equilibrium concentrations ($cX_{eq}$) according to the equilibrium constant ($K_{eq}(T)$) of this reaction:

$$K_{eq}(T) = \frac{cCr_{eq}(T)}{cCrn_{eq}(T)} = \frac{k_1(T)}{k_2(T)}. \qquad \text{Equation 3}$$

The equilibrium constant can also be expressed in terms of rate constants $k_1(T)$ and $k_2(T)$ for the forward and backward reactions (the individual arrows) involved in the conversion reaction in Scheme 1. The rate constants are temperature dependent, but are not necessarily equally dependent. Therefore, the equilibrium constant $K_{eq}(T)$ of the conversion reaction (and hence the equilibrium concentration of Crn and Cr) will also be temperature dependent.

The temperature dependency of the rate constants is dictated by the Arrhenius-equation:

$$k_i(T_t) = A_i \cdot \exp\left(\frac{\beta_i}{T_t}\right) = \exp\left(\alpha_i + \frac{\beta_i}{T_t}\right), \text{ where } \alpha_i = \ln A_i \qquad \text{Equation 4}$$

The subscript on the temperature T is here used as a short hand notation to indicate that it may be a function of time t. $\alpha_i$ and $\beta_i$ are the relevant Arrhenius parameters for the reaction in consideration, which are known with a very high degree of accuracy.

The above reactions are spontaneously taking place in calibrator Cal2 and Cal3 from the moment when Cr and/or Crn are added during the production process. Therefore, the actual concentrations of Cr and Crn in the calibrators in a solution pack strongly depend on the time passed since production and on the temperature profile $T_{profile}(t)$ experienced by the individual solution pack during that time span.

Table 3 shows the changes in concentration of Cr and Crn in Cal2 and Cal3 as a function of time and the temperature profile:

TABLE 3

| At time: t > $t_{production}$ | Cal2 | Cal3 |
|---|---|---|
| cCr [µM] | $\Delta cCrn_{Cal2}(t, T_{profile}(t))$ | $500 - \Delta cCr_{Cal3}(t, T_{profile}(t))$ |
| cCrn [µM] | $500 - \Delta cCrn_{Cal2}(t, T_{profile}(t))$ | $\Delta cCr_{Cal3}(t, T_{profile}(t))$ |

In Table 3, $\Delta cCrn_{Cal2}$ is the change in the Crn concentration in Cal2 up to time t due to its one to one conversion into Cr; and $\Delta cCr_{Cal3}$ is the change in the Cr concentration in Cal3 up to time t due to its one to one conversion into Crn.

The concentration change (dcCrn) of cCrn during an infinitesimal time span (dt) obeys the following differential equation, also known as the rate equation:

$$\frac{dcCrn}{dt} = k_2(T_t) \cdot cCr - k_1(T_t) \cdot cCrn, \qquad \text{Equation 5}$$

Combining the reaction rate equations (Equation 5), with the Arrhenius equations (Equation 4) and the two-temperature model, provides the analytic expressions $cCr_{Cal\,\#}^{model}(t_1)$ and $cCrn_{Cal\,\#}^{model}(t_1)$, which are respectively the Cr and Crn concentrations in calibrator "Cal #" as functions of the time $t_1$ spent at the initial temperature $T_1$, typically the lower temperature.

If each of the true temperature profile ($T_t = T_{profile}(t)$); the relevant Arrhenius-parameters ($\alpha_i$ and $\beta_i$) for the above reaction; and the starting concentrations $cCr_{Cal\,\#}^0$ and $cCrn_{Cal\,\#}^0$ of Cr and Crn in calibrator Cal # at time t=0, are known, then very accurate estimates of the true Cr and Crn concentrations in that calibrator at any time afterwards can be obtained by integration of the rate equation.

The true temperature profile experienced by the calibration solutions during storage, transport, storage at the customer, and usage, may not be known by the end user if no record of temperature variation is available. Although the exact temperature profile may be unknown, there are several variables independent of one another that can be measured to reveal details of the conditions. Therefore, in order to obtain a sufficiently accurate estimate of the unknown true temperature profile we utilize all available degrees-of-freedom (DOFs) in the cCrn measuring system, that are not utilized for other purposes, e.g., for calibrating the Crea A and Crea B sensors.

The measurements with the Crea A and Crea B sensors on the two calibrations solutions Cal2 and Cal3 result in 4 sensors signals, i.e. 4 available DOFs. According to Table 2 and its supporting text, 3 out of the 4 available DOFs are allocated for sensor calibration purposes, which leave one unused DOF in surplus: the Crea A signal on Cal2. This single DOF can be utilized to determine the value of an "unknown" entity in the same manner as the other 3 DOFs will be utilized for determining the 3 "unknown" sensor sensitivities.

Figure 3:
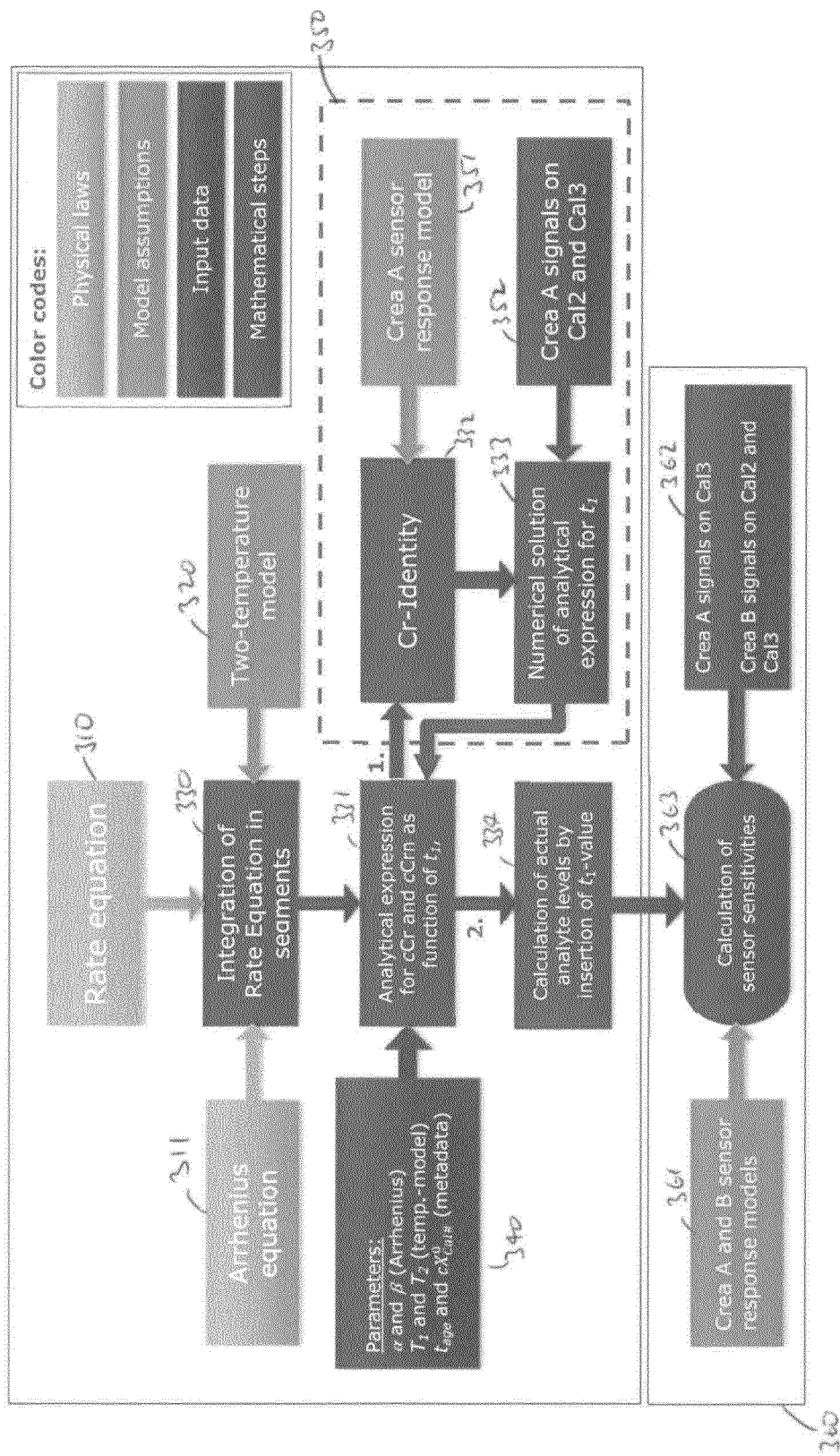
FIG. 3 is a flow chart showing the derivation of the proposed method.

FIG. 3 is a flow chart showing the step-by-step derivation for the proposed method of determining analyte levels in the calibrators and subsequently calibrating the sensors.

As discussed above, the rate equation 310 (Equation 5) is combined with the Arrhenius equation 311 (Equation 4) and the temperature model 320. To choose an appropriate temperature model, one needs to be aware of the general pattern of temperature fluctuations that are to be expected. Table 1 provides an example of this general pattern as it indicates the different conditions (storage at production, transport, storage at customer, and usage) that the calibrations solutions may undergo. The table also shows the temperature ranges that the calibration solutions are expected to experience, and it indicates what time periods these solutions are expected to remain at these conditions.

The chosen temperature model may have an initial temperature ($T_1$) at an initial time ($t_{production}$ or t=0), an end temperature ($T_2$) at the time of calibration ($t_{age}$), and an intermediate time point ($t_1$) at which the temperature changes from the initial to the end temperature. While the initial time and end time will be known, and the initial temperature and end temperature are either known or estimated, the intermediate time $t_1$ may not be known at all. In such a scenario, the available DOF can be used to determine this intermediate time $t_1$.

The skilled person would look at the data available, and construct a temperature model accordingly. Where there is one available DOF, the temperature model would be constructed so that there is only one unknown, such as intermediate time $t_1$. Where there is more than one available DOF, a temperature model can be constructed with as many unknowns as there are available DOFs.

In the embodiment described above, the available DOF is used to determine the variable parameter $t_1$, in a temperature model comprising two known (or estimated) temperatures and the time $t_1$ at which the temperature changes between the two. Another possible use of the available DOF is to determine an average conversion temperature being used throughout the whole timespan $t_{age}-t_{production}$, in a temperature model comprising a single unknown temperature as the variable parameter.

In the example presented herewith, the true temperature profile $T_{profile}(t)$ can be modelled by a two-temperature model, which depends on initial and end temperatures $T_1$ and $T_2$, end time $t_{age}$ and intermediate time $t_1$ (and implicitly initial time $t_0$=0). Given the general pattern identified, the true temperature profile can be modelled as a simple step change from an initial temperature to an end temperature at the intermediate time $t_1$. This model can be represented as:

$$T^{model}_{profile}(t; T_1, T_2, t_1, t_{age}) = \begin{cases} T_1, & 0 \leq t \leq t_1 \\ T_2, & t_1 < t \leq t_{age} \end{cases} \quad \text{Equation 6}$$

Temperatures $T_1$ and $T_2$ can, in principle, be chosen arbitrarily. However, to ensure that the model can encompass all possible temperature scenarios, the temperatures $T_1$ and $T_2$ may be set to match the expected temperature ranges. Using the expected patterns set out in Table 2, the temperatures may be set to the minimum (2° C.) and maximum temperatures (32° C.) specified in any of the three preliminary temperature intervals in Table 2. The initial temperature $T_1$ may be representative of the expected cold storage temperature of the calibration solutions, and the end temperature $T_2$ may be representative of the temperature the calibration solutions are expected to experience during transportation and/or during use. As such, the initial temperature and end temperature may not be the actual temperature at the initial time $t_1$ and end time $t_{age}$ respectively.

The parameter $t_1$ is an unknown amount of time spent at the temperature $T_1$. The parameter $t_{age}$ is the age of the solution pack relative to the time point t=0 when the analyte levels ($cCr_{Cal2}^0$, $cCrn_{Cal2}^0$, $cCr_{Cal3}^0$, $cCr_{Cal3}^0$) in the calibrators are measured using a reference method. The analyte levels and the absolute time point at which they were measured may be stored electronically in each individual solution pack and so that they can be easily input upon analysis.

At step 330, the combination of the rate equation 310 (Equation 5), the Arrhenius equation 311 (Equation 4) and the temperature model 320 is solved analytically. This is done by solving the resultant differential equation twice, i.e., in segments of constant temperatures $T_1$ and $T_2$ with corresponding time spans $t_1$ and $t_2=t_{age}-t_1$, respectively, and by using the appropriate starting conditions in each segment. This leads to the following equations for the Cr and Crn concentrations in a given calibrator ("Cal #") as function of $t_1$:

$$cCr^{model}_{Cal\#}(t_1; t_{age}, T_1, T_2) = \quad \text{Equation 7}$$
$$\frac{k_1(T_2)}{K(T_2)} \cdot c^{tot}_{Cal\#} + \left(\left(\frac{k_2(T_1)}{K(T_1)} - \frac{k_2(T_2)}{K(T_2)}\right) \cdot c^{tot}_{Cal\#} - \right.$$
$$\left. \left(cCr^0_{Cal\#} - \frac{k_1(T_1)}{K(T_1)} \cdot c^{tot}_{Cal\#}\right) \cdot e^{-t_1 K(T_1)} \right) \cdot e^{-(t_{age}-t_1)K(T_2)}$$

$$cCrn^{model}_{Cal\#}(t_1; t_{age}, T_1, T_2) = \quad \text{Equation 8}$$
$$\frac{k_2(T_2)}{K(T_2)} \cdot c^{tot}_{Cal\#} + \left(\left(\frac{k_1(T_1)}{K(T_1)} - \frac{k_2(T_2)}{K(T_2)}\right) \cdot c^{tot}_{Cal\#} + \right.$$
$$\left. \left(cCrn^0_{Cal\#} - \frac{k_2(T_1)}{K(T_1)} \cdot c^{tot}_{Cal\#}\right) \cdot e^{-t_1 K(T_1)} \right) \cdot e^{-(t_{age}-t_1)K(T_2)}$$

Where $c_{Cal\#}^{tot} = cCr_{Cal\#}^0 + cCrn_{Cal\#}^0$ and $K(T)=k_1(T)+k_2(T)$ are constants. Equation 7 gives the concentration of Cr at end time $t_{age}$. Many of the parameters 340 of the Equations 7 and 8 are already known, and the unknown variable is $t_1$. The values $k_1$, $k_2$ and $K$ can be determined from the Arrhenius equations, where $\alpha$ and $\beta$ are well values that are known to a high accuracy. The concentrations $cCr_{Cal\#}^0$, $cCrn_{Cal\#}^0$ and $c_{Cal\#}^{tot}$ are the known concentrations from measuring the solutions at time t=0. Temperatures $T_1$ and $T_2$ and known from the temperature-model used, and $t_{age}$ is known from being the time since production of the calibration solutions. Therefore, Equations 7 and 8 are the expressions at step 331, but before the actual concentrations can be calculated, the unknown variable $t_1$ needs to be determined from the steps in box 350.

From the sensor response model 351 in Equation 1, the following universally valid relationship can readily be derived for measurements with the uncalibrated Crea A sensor on both calibrators at a given time, e.g. $t=t_{age}$:

$$\frac{I^A_{Cal2}(t_{age})}{cCr_{Cal2}(t_{age})} = \frac{I^A_{Cal3}(t_{age})}{cCr_{Cal3}(t_{age})} \quad \text{Equation 9}$$

The relationship of Equation 9 is valid for an uncalibrated Crea A sensor as no calibration parameters, i.e. the Cr sensitivity $S_{Cr}^A$, enter the equation. Equation 9 states that the ratio between the Crea A sensor signal and the Cr concentration measured for one calibration solution has the same value as for the other calibration solutions at a given time.

The analytical expression for $cCr_{Cal\ \#}^{model}$ and $cCrn_{Cal\ \#}^{model}$ in Equations 7 and 8 can now be inserted into Equation 9 to form the "Cr-identity" 332 Equation 10.

$$\frac{I_{Cal2}^{A}(t_{age})}{I_{Cal3}^{A}(t_{age})} = \frac{cCr_{Cal2}^{model}(t_1; t_{age}, T_1, T_2)}{cCr_{Cal3}^{model}(t_1; t_{age}, T_1, T_2)} \quad \text{Equation 10}$$

The raw outputs of the Crea A sensor for the two calibration solutions at the end time can be input into the left-hand side of Equation 10. The right-hand side of the equation is a non-linear function of the one remaining unknown variable $t_1$, and is a monotonic function within most realistic temperature and time ranges. As a monotonic function, only one solution for $t_1$ exists, so Equation 10 can be solved by numerical methods to find $t_1$ at step 333. As a result, the ratio between the raw signals of the Crea A sensor leads to one possible value of $t_1$, and hence one possible temperature profile approximating the true temperature profile.

Once the value of $t_1$, and consequently the temperature model, are known Equations 7 and 8 for the concentrations of the calibration solutions can be solved 334. Specifically, the Cr concentrations $cCr_{Cal2}$ and $cCr_{Cal3}$, and the Crn concentrations $cCrn_{Cal2}$ and $cCrn_{Cal3}$ can be determined for the calibration solutions at the end time.

Once the concentrations of Cr and Crn have been estimated for the calibration solutions at the end time, it is possible to compare these concentrations with raw sensor readings of the calibrations solutions to determine the sensitivities, and hence calibrate 360, the sensors.

Equations 1 and 2 provide the sensor response models for the Crea A and Crea B sensors respectively. At step 361 these sensor response models can be used to derive the following relationships:

$$S_{Cr}^{A} = \frac{I_{Cal3}^{A}}{cCr_{Cal3}} \quad \text{Equation 11}$$

$$S_{Cr}^{B} = \frac{I_{Cal2}^{B} \cdot cCrn_{Cal3} - I_{Cal3}^{B} \cdot cCrn_{Cal2}}{cCr_{Cal2} \cdot cCrn_{Cal3} - cCr_{Cal3} \cdot cCrn_{Cal2}} \quad \text{Equation 12}$$

$$S_{Crn}^{B} = \frac{I_{Cal3}^{B} \cdot cCr_{Cal2} - I_{Cal2}^{B} \cdot cCr_{Cal3}}{cCr_{Cal2} \cdot cCrn_{Cal3} - cCr_{Cal3} \cdot cCrn_{Cal2}} \quad \text{Equation 13}$$

The calibration concentrations can be determined from step 334, and the raw signals for the Crea A sensor at Cal3 and the Crea B sensor at Cal2 and Cal3 can be determined at step 362. These values can be substituted into Equations 11, 12 and 13 at step 363 to calculate the sensitivities of the Crea A sensor for Cr, and the Crea B sensor for Cr and Crn. With these sensitivities, it is possible to accurately measure the concentrations of Cr or Crn in any given sample.

Figure 4:
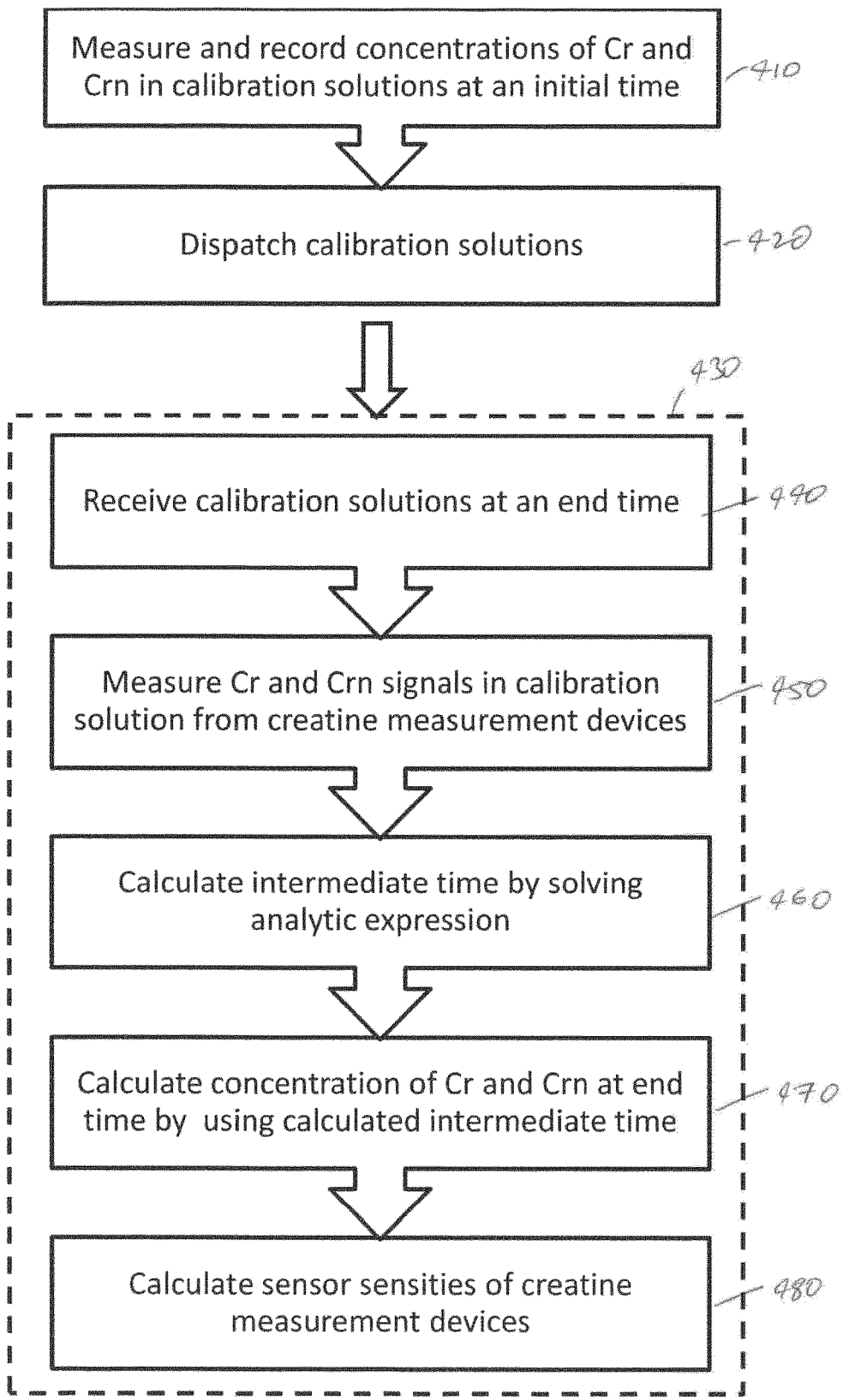
FIG. 4 is a flow chart outlining the steps of the proposed method.

While FIG. 3 outlines the steps for deriving the proposed method, FIG. 4 summarises the steps for carrying out an example embodiment of the proposed method. The proposed method is not limited to the ordering of the steps shown in FIG. 4, nor is the method envisioned to be solely limited to this example embodiment provided.

At step 410, the concentrations of the Cr and Crn in the calibration solutions are measured and recorded at an initial time. The initial time may be just after production of the solutions and/or at any appropriate time before dispatch of the calibration solutions. The concentrations may be measured using a range of techniques and known sensors, such as by high-performance liquid chromatography (HPLC).

The concentrations may be recorded by any means that allow the end user to use these recorded concentrations in the subsequent calculations. For example, the concentrations may be stored in writing on the calibration pack, or may be stored electronically at a server, or may be stored electronically at the calibration pack itself so that a calibration machine can automatically read the stored variable. Similarly, the packs may be time-stamped so that the initial time will be known when performing the subsequent calculations.

At step 420 the calibration solutions are dispatched to the end consumer. From this point, the actual temperatures the calibration solutions are stored at may not be known.

Box 430 illustrates the steps that can be taken by an end user attempting to calibrate the Cr and Crn sensors, starting with receiving the calibration solutions and starting the calibration process at an end time (also referred to as $t_{age}$) 440.

At step 450, the raw Cr and Crn signals in the calibration solutions are measured by the sensors. These raw signals are the current outputs $I_{Cal2}^{A}(t_{age})$, $I_{Cal3}^{A}(t_{age})$, $I_{Cal2}^{B}(t_{age})$ and $I_{Cal3}^{B}(t_{age})$ of the sensors.

At step 460, the temperature model is determined. In the example of a two-temperature model, this involves calculating the intermediate time $t_1$ by solving Equation 10 for $t_1$. To perform this calculation, the Arrhenius values for the relevant reactions need to be known, along with the initial time and initial concentrations that were recorded at step 410.

At step 470, the actual concentrations of Cr and Crn in the calibration solutions are calculated by solving Equations 7 and 8 using the temperature model determined at step 460.

At step 480, the sensor outputs calculated in step 450 (specifically, $I_{Cal3}^{A}(t_{age})$, $I_{Cal2}^{B}(t_{age})$ and $I_{Cal3}^{B}(t_{age})$) and the concentrations calculated at step 470 are substituted into Equations 11 to 13 to determine the sensor sensitivities, thereby calibrating the sensors.

The steps performed at box 430 may be performed manually by an end user. Alternatively, some or all of the steps at box 430 can be automated by a system. For example, a calibration system may take the calibration pack and automatically read electronic data indicating the initial concentrations and initial time. The calibration system may measure all the raw sensor outputs as indicated in steps 450 and 470. The calibration system may contain an electronic device with a processor for performing the calculations of steps 460, 470 and 480. Computer software may be supplied in a computer-readable medium that the user can install on their own computer to automatically perform any of the calculations of the method.

Figure 5:
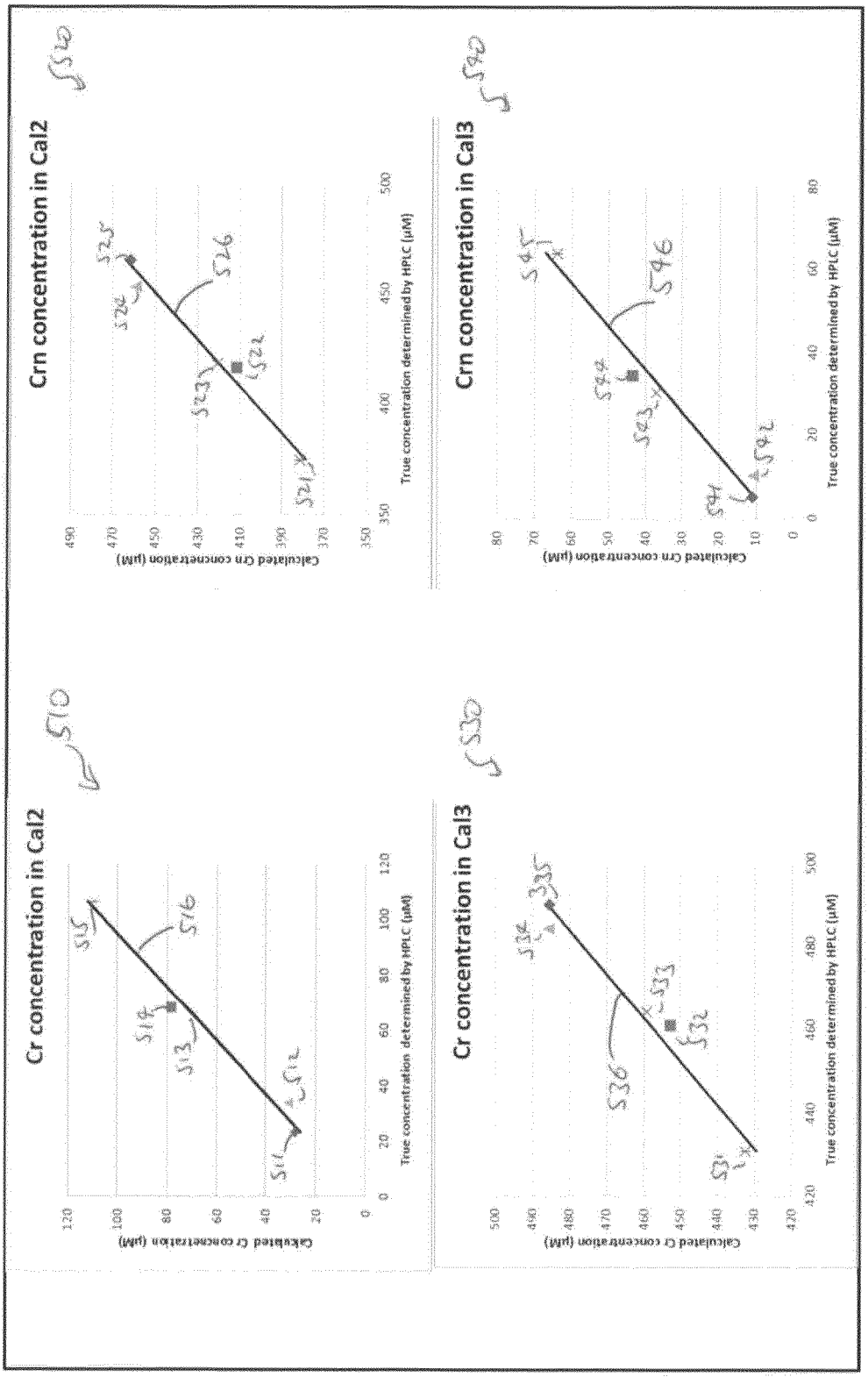
FIG. 5 is a series of graphs comparing the concentrations in the calibration solutions with the concentrations calculated in accordance with an example embodiment of the proposed method.

While the temperature model used to calibrate the sensors is only an estimation of the true temperature profile of the calibration solutions, the proposed solution provides very accurate results. FIG. 5 shows a number of graphs comparing the actual concentrations of the calibration solutions (using HPLC, for example) with the concentrations calculated with the proposed method.

The tests were performed for Cal2 and Cal3 solutions stored at different temperatures for a variety of time spans, which correspond to realistic time/temperature scenarios for the solution packs, but also to extreme scenarios which exceed the specified time/temperature ranges in Table 1.

Data points 511, 521, 531 and 541 are for calibration solutions stored at 10° C. for 53 days. Data points 512, 522, 532 and 542 are for calibration solutions stored for 53 days at 10° C., 15 days at 32° C., and 34 days at 10° C. Data points 513, 523, 533 and 543 are for calibration solutions stored for 53 days at 10° C., 15 days at 6° C., 29 days at 10°

C., and 20 days at 6° C. Data points 514, 524, 534 and 544 are for calibration solutions stored for 53 days at 10° C., 15 days at 25° C., 29 days at 10° C., and 20 days at 25° C. Data points 515, 525, 535 and 545 are for calibration solutions stored for 53 days at 10° C., 32 days at 32° C., 29 days at 10° C., and 20 days at 32° C.

Graph 510 shows the calculated and actual Cr concentrations in the Cal2 solution at different temperature conditions. The linear trend line 516 (formula y=1.0317x+2.0703) indicates a linear relationship between the calculated and actual concentrations, with an $R^2$ value of 0.98. Graph 520 shows the calculated and actual Crn concentrations in the Cal2 solution at different temperature conditions. The linear trend line 526 (formula y=0.9466x+24.0) indicates a linear relationship between the calculated and actual concentrations, with an $R^2$ value of 0.9786. Graph 530 shows the calculated and actual Cr concentrations in the Cal3 solution at different temperature conditions. The linear trend line 536 (formula y=0.9522x+17.951) indicates a linear relationship between the calculated and actual concentrations, with an $R^2$ value of 0.97. Graph 540 shows the calculated and actual Crn concentrations in the Cal3 solution at different temperature conditions. The linear trend line 546 (formula y=0.9621x+5.5329) indicates a linear relationship between the calculated and actual concentrations, with an $R^2$ value of 0.97.

These graphs show that even though the temperature model is only an estimate of the true temperature profile, the concentrations calculated with the proposed method are consistently close to the actual concentrations.

Figure 6:
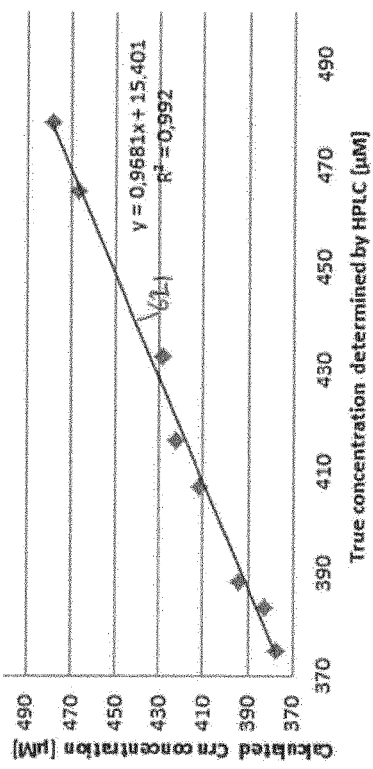
FIG. 6 is a series of graphs comparing the concentrations in the calibration solutions with the concentrations calculated in accordance with a further example embodiment of the proposed method.
Figure 6:
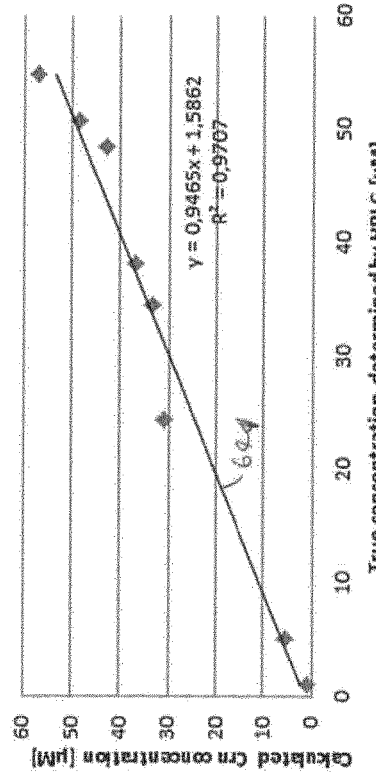
Figure 6:
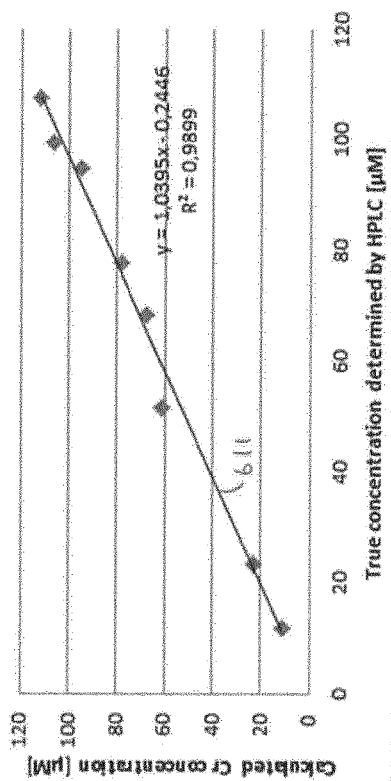
Figure 6:
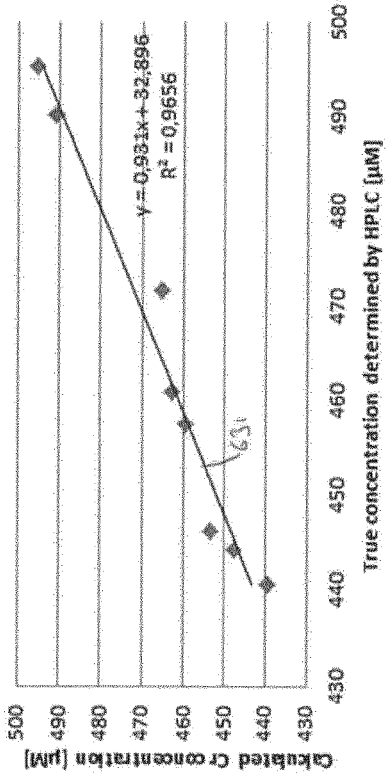

FIG. 6 shows a number of graphs comparing the actual concentrations of the calibration solutions (using HPLC, for example) with the concentrations calculated with the example embodiment using a temperature logger to generate a temperature model.

The tests were performed for Cal2 and Cal3 solutions stored at different temperatures for a variety of time spans, which correspond to realistic time/temperature scenarios for the solution packs, but also to extreme scenarios which exceed the specified time/temperature ranges in Table 1.

Graph 610 shows the calculated Cr concentrations in the Cal2 solution compared to the actual concentrations. The linear trend line 611 (formula y=1.0395x−0.24446) indicates a linear relationship between the calculated and actual concentrations, with an $R^2$ value of 0.9899. Graph 620 shows the calculated Crn concentrations in the Cal2 solution compared to the actual concentrations. The linear trend line 621 (formula y=0.9681x+15.401) indicates a linear relationship between the calculated and actual concentrations, with an $R^2$ value of 0.992. Graph 630 shows the calculated Cr concentrations in the Cal3 solution compared to the actual concentrations. The linear trend line 631 (formula y=0.931x+32.896) indicates a linear relationship between the calculated and actual concentrations, with an $R^2$ value of 0.9656. Graph 640 shows the calculated Crn concentrations in the Cal3 solution compared to the actual concentrations. The linear trend line 641 (formula y=0.9465x+1.5862) indicates a linear relationship between the calculated and actual concentrations, with an $R^2$ value of 0.9707.

These graphs show that using temperature probes to record historic changes in temperature can lead to very accurate calculations for Cr and/or Crn concentrations.

It is to be understood that the present disclosure includes permutations of combinations of the optional features set out in the embodiments described above. In particular, it is to be understood that the features set out in the appended dependent claims are disclosed in combination with any other relevant independent claims that may be provided, and that this disclosure is not limited to only the combination of the features of those dependent claims with the independent claim from which they originally depend.

The invention claimed is:

1. A method for recalibrating the sensitivity of one or more sensors in a measuring device for measuring concentration of creatinine (Crn) using one or more calibration solutions, wherein the method comprises:
   providing the measuring device for determining concentration of Crn in a solution, wherein the measuring device comprises the one or more sensors having the sensitivity in need of recalibration;
   providing the one or more calibration solutions comprising one or more of a creatine (Cr) calibration solution and/or one or more of a Crn calibration solution for the one or more sensors, wherein the one or more calibration solutions has been stored at at least one unknown temperature after an initial time;
   receiving concentrations at the initial time of Cr and/or Crn in the one or more calibration solutions;
   receiving outputs of the measuring device at an end time;
   calculating concentration of Cr and/or Crn in the one or more calibration solutions at the end time using a two-temperature temperature model, rate equations for an equilibrium reaction of Cr and Crn, and the Arrhenius equation;
      wherein the two-temperature temperature model indicates an estimation of temperature of the one or more calibration solutions from the initial time to the end time, and wherein the two-temperature temperature model includes a variable parameter, and
      wherein the two-temperature temperature model is determined by at least calculating the variable parameter,
      wherein said calculating the variable parameter comprises solving an analytic expression comprising the rate equations for the equilibrium reaction of Cr and Crn, the two-temperature temperature model, and the outputs of the measuring device;
   determining the sensitivity of the one or more sensors based on a relationship between the outputs of the measuring device and the calculated concentration of Cr and/or Crn; and
   recalibrating the sensitivity of the one or more sensors for subsequent determination of the concentration of Cr and/or Crn in a sample.

2. The method of claim 1, wherein one or more of the one or more sensors is a sensor for measuring creatine in the one or more calibration solutions.

3. The method of claim 1, wherein one or more of the one or more sensors is a sensor for measuring Crn in the one or more calibration solutions.

4. The method of claim 1, wherein one of the one or more sensors is a sensor for measuring Cr and Crn in the one or more calibration solutions.

5. The method of claim 1, wherein the measuring device is an amperometric measuring device.

6. The method of claim 1, wherein the analytic expression is derived from an integration of the rate equations for the equilibrium reaction of Cr and Crn for the two-temperature temperature model, wherein rate constants in the rate equations for the equilibrium reaction of Cr and Crn are derived from Arrhenius equations.

7. The method of claim 1, wherein the two-temperature temperature model comprises an average temperature from the initial time to the end time, and the variable parameter is the average temperature.

8. The method of claim 1, wherein the two-temperature temperature model comprises a temperature at the initial time and a different temperature at an intermediate time, and wherein the variable parameter is the intermediate time.

9. The method of claim 1, further comprising determining concentrations of Cr and/or Crn in the sample based on the determined sensor sensitivities of the measuring device and the outputs of the measuring device.

10. The method of claim 1, wherein the end time is greater than 14 days after the initial time.

11. A computer readable medium comprising instructions which, when executed by one or more processors of an electronic device, cause the electronic device to operate in accordance with the method of claim 1.

12. An electronic device comprising:
- one or more processors; and
- memory comprising instructions which when executed by one or more of the one or more processors cause the electronic device to operate in accordance with the method of claim 1.

* * * * *